US009615759B2

(12) United States Patent
Hurezan

(10) Patent No.: US 9,615,759 B2
(45) Date of Patent: Apr. 11, 2017

(54) DEVICES AND METHODS FOR ECG GUIDED VASCULAR ACCESS

(75) Inventor: Isabella Barbara Hurezan, Bucharest (RO)

(73) Assignee: Bard Access Systems, Inc., Salt Lake City, UT (US)

( * ) Notice: Subject to any disclaimer, the term of this patent is extended or adjusted under 35 U.S.C. 154(b) by 874 days.

(21) Appl. No.: 13/507,545

(22) Filed: Jul. 9, 2012

(65) Prior Publication Data

US 2013/0018248 A1 Jan. 17, 2013

Related U.S. Application Data

(60) Provisional application No. 61/457,934, filed on Jul. 12, 2011.

(51) Int. Cl.
*A61B 5/0408* (2006.01)
*A61B 5/0492* (2006.01)
*A61B 5/0402* (2006.01)
*A61B 5/00* (2006.01)
*A61B 5/06* (2006.01)

(52) U.S. Cl.
CPC .............. *A61B 5/0402* (2013.01); *A61B 5/06* (2013.01); *A61B 5/6876* (2013.01)

(58) Field of Classification Search
CPC ..... A61B 5/042; A61B 5/0492; A61B 5/6848; A61B 5/6849; A61B 5/685; A61B 5/6852; A61B 5/6885; A61B 2560/0486; A61B 2562/125; A61B 2562/16; A61B 2562/168; A61B 2562/182; A61B 2562/22; A61B 2562/222; A61B 2562/225; A61B 2562/227; A61B 5/6865; A61B 5/6876; A61M 5/315
USPC ................ 600/372, 373, 397, 381, 546, 548
See application file for complete search history.

(56) References Cited

U.S. PATENT DOCUMENTS

| | | | | |
|---|---|---|---|---|
| 3,682,162 A | * | 8/1972 | Colyer | A61B 5/042 600/373 |
| 4,644,960 A | * | 2/1987 | Johans | A61B 5/042 604/20 |
| 5,078,714 A | * | 1/1992 | Katims | A61M 25/0105 604/264 |
| 5,306,236 A | * | 4/1994 | Blumenfeld | A61B 5/0492 600/546 |
| 6,152,933 A | * | 11/2000 | Werp | A61M 27/006 604/165.01 |

(Continued)

*Primary Examiner* — Lee S Cohen
*Assistant Examiner* — Erin M Cardinal
(74) *Attorney, Agent, or Firm* — Rutan & Tucker, LLP

(57) ABSTRACT

A new device and a method are provided which allow for making an electrical connection between an electrolyte and an electric wire. A new connector is provided which allows to be used by a single sterile operator. A new valved device is provided which allows for maintaining the integrity and the pressure of a saline column in the central venous line. A new device is provided which allows for automatically maintaining a continuous flush of a saline syringe in order to allow for keeping the valves of central venous lines open and capable of electric conduction. A new syringe is provided which allows for simultaneous electrical connection between the fluid in the syringe and an electrical wire. Several new methods are provided for making an electrical connection to a central venous line during and after the catheter placement procedure.

9 Claims, 14 Drawing Sheets

(56) References Cited

U.S. PATENT DOCUMENTS

| | | | | |
|---|---|---|---|---|
| 6,298,256 | B1* | 10/2001 | Meyer | A61B 5/05 600/373 |
| 6,459,917 | B1* | 10/2002 | Gowda | A61B 5/14528 600/345 |
| 7,120,487 | B2* | 10/2006 | Nelson | A61M 25/0606 604/158 |
| 7,717,932 | B2* | 5/2010 | McFarlin | A61B 17/1622 606/170 |
| 9,125,578 | B2* | 9/2015 | Grunwald | A61B 5/04017 |
| 2008/0086042 | A1* | 4/2008 | Brister | A61B 5/14532 600/347 |
| 2010/0318026 | A1* | 12/2010 | Grunwald | A61B 5/04017 604/95.05 |
| 2011/0288574 | A1* | 11/2011 | Curry | A61B 5/157 606/185 |

* cited by examiner

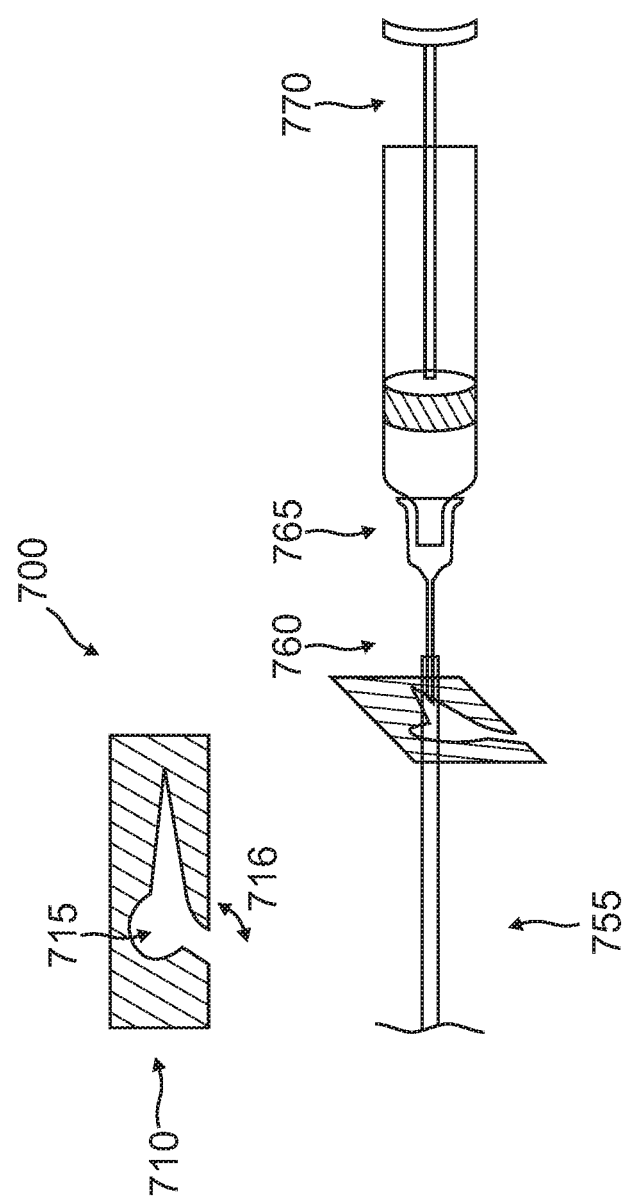

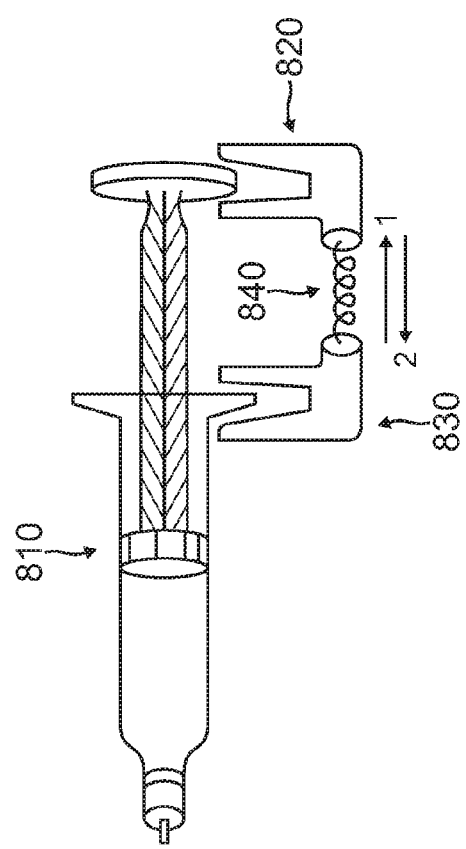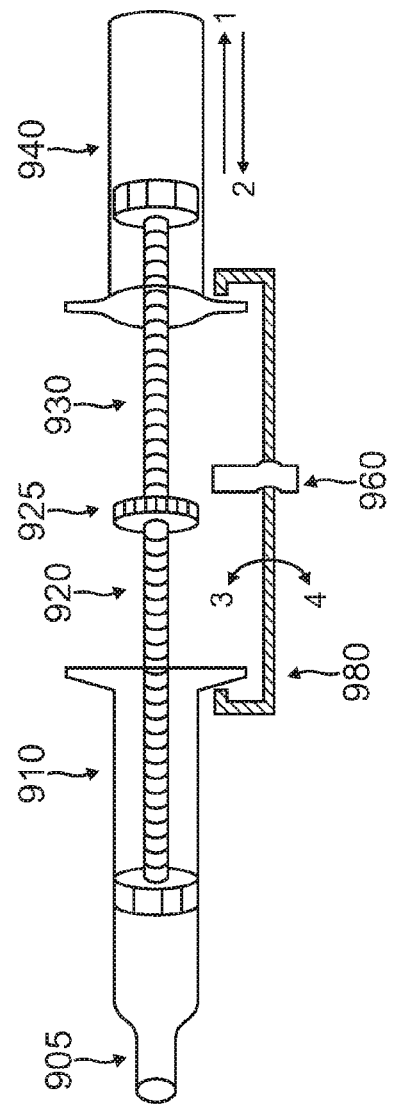

DEVICES AND METHODS FOR ECG GUIDED VASCULAR ACCESS

CROSS-REFERENCE TO RELATED APPLICATIONS

This application claims priority to U.S. Provisional Patent Application Ser. No. 61/457,934 filed on Jul. 12, 2011, the disclosure of which is incorporated herein by reference in its entirety.

FIELD OF THE INVENTION

The invention describes devices and methods for electrically connecting catheters including central venous access devices, e.g., CVC, PICC, implantable ports, hemodialysis catheters, stylets, access needles, introducers, guidewires, etc. to a system which allows for electrical patient data acquisition, e.g., an ECG monitor.

BACKGROUND OF THE INVENTION

Tip position of a central venous access is of paramount importance and should be verified before starting infusion. Intra-procedural methods for verifying the location of the tip are to be preferred, since they avoid the risks, delays and costs of repositioning the tip. Among the intra-procedural methods, the electrocardiography (ECG) method has many advantages since it is as accurate as fluoroscopy, but simpler, more readily available, less expensive, safer and more cost-effective. When dealing with the insertion of peripherally inserted central catheters (PICC), the ECG method (using the column of saline technique) virtually has no risk of false positives. The ECG method removes the need for the post-procedural chest x-ray, as long as there is no expected risk of pleuropulmonary damage to be ruled out (example: ultrasound guided central venipuncture for central venous catheter insertion or any kind of PICC insertion). In conclusion, evidence is mounting that the ECG method may be a valid and cost-effective alternative to the standard radiological control of the location of the tip of any central venous access device (VAD), and that will rapidly become the preferential method for confirming the tip position during PICC insertion.

Currently, the verification of the tip location of a central venous line may be achieved at the end of the procedure using various imaging techniques, such as MR, CT scan, standard trans-thoracic echocardiography, or TEE (transesophageal echocardiography). The most commonly used "post-procedural" method (and one of the most cost-effective) is the standard post-procedural chest x-ray. However, checking the position of the tip of the catheter during the procedure is preferable to a post-procedural control (6). During catheter insertion, the correct position of the catheter tip can be checked by several different methods:
 intra-operative fluoroscopy and/or intra-operative control radiography;
 standard trans-thoracic echocardiography or transesophageal echocardiography;
 the electrocardiographic method (intracavitary ECG);
 electromagnetic and infrared light guidance
 Doppler ultrasound Each of these methods has certain advantages and disadvantages, such that today, the most widely accepted and used method is the post-procedural x-ray although, as it has been shown by different studies, the ECG methods could become the method of choice. The present invention describes several new devices for central venous lines guidance optimized for the ECG method.

The present invention addresses the existing clinical and technical problems in several ways. In one aspect of the invention a new device and a method are described which allow for making an electrical connection between an electrolyte and an electric wire. In one embodiment, the electric wire is shielded. In another aspect of the invention a new connector is described which allows to be used by a single sterile operator. In another aspect of the invention a valved device is described which allows for maintaining the integrity and the pressure of a saline column in the central venous line. In another aspect of the invention a device is described which allows for automatically maintaining a continuous flush of a saline syringe in order to allow for keeping the valves of central venous lines open and capable of electric conduction. In another aspect of the invention several devices are described which allow for making a selective electrical connection of certain elements of central venous lines to a connecting wire while isolating other certain elements of central venous lines from electrical contact. In another aspect of the invention a syringe is described which allows for simultaneous electrical connection between the fluid in the syringe and an electrical wire. The devices described in the present invention can be used for guiding and verifying the catheter tip placement using the ECG method during the placement procedure and any time post-procedurally.

SUMMARY OF THE INVENTION

This invention relates to the field of ECG-guided placement of catheters including central venous lines, e.g., central venous catheters (CVC), implantable ports, peripherally inserted central catheters (PICC), hemodialysis catheters, stylets, access needles, introducers, guidewires, etc. It introduces several new vascular access devices allowing for safe, effective, and user friendly connection between central venous catheters and an ECG monitor or any other system capable of acquiring and displaying electrical signals of the heart.

In one aspect of the invention a new device and a method are described which allow for making an electrical connection between an electrolyte and an electric wire. In another aspect of the invention a new connector is described which allows to be used by a single sterile operator. In another aspect of the invention a valved device is described which allows for maintaining the integrity and the pressure of a saline column in the central venous line. In another aspect of the invention a device is described which allows for automatically maintaining a continuous flush of a saline syringe in order to allow for keeping the valves of central venous lines open and capable of electric conduction. In another aspect of the invention several devices are described which allow for making a selective electrical connection of certain elements of central venous lines to a connecting wire while isolating other certain elements of central venous lines from electrical contact. In another aspect of the invention a syringe is described which allows for simultaneous electrical connection between the fluid in the syringe and an electrical wire. In another aspect of the invention several methods are described for making an electrical connection to a central venous line during and after the placement procedure.

BRIEF DESCRIPTION OF THE DRAWINGS

FIG. 7: Method for maintaining saline column integrity

FIG. 8: Device for opening the distal valves of a catheter using saline

FIG. 9: Another embodiment of a device for opening the distal valves of a catheter using saline

DETAILED DESCRIPTION

Figure 1A:
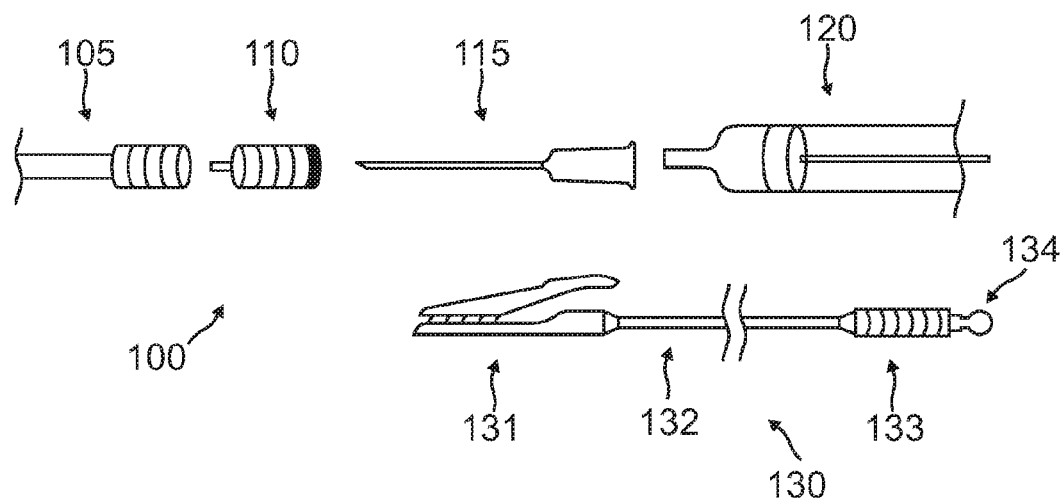
FIGS. 1A-1C: Method to make an electrical connection to a catheter using saline solution.

The invention will now be described with reference to the drawing figures, in which like reference numerals refer to like parts throughout.

Figure 1B:
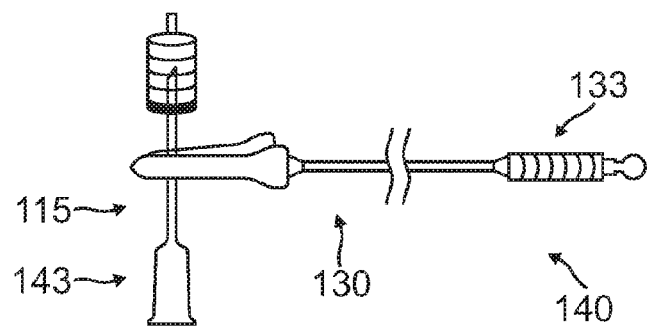
Figure 1C:
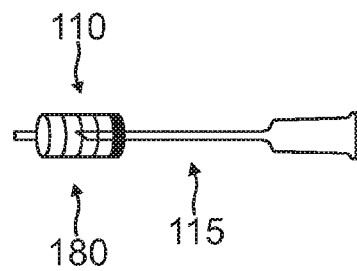

FIG. 1 illustrates a method to make an electrical connection to a catheter using saline solution. The method uses a group of devices (100) consisting of: a catheter with a female Luer lock (105), a heparin cap or an equivalent valved cap (110), a needle (115), a syringe (120) and a connector cable (130). The connector cable consists of an alligator clip (131) at one end, a shielded or non-shielded cable (132) and a connector to be connected to an ECG cable at the other end (133). The connector (133) has a metal component (134) which can be connected to the clip of an ECG cable.

The methods consist of the following steps:
1. Insert the needle (115) into the heparin cap (110). Connect the assembly (180) to the hub (Luer lock) of the catheter (105). Alternatively, the heparin cap (110) can be connected to the Luer lock of the catheter first, and then the needle 115 inserted into the heparin cap (110).
2. Connect the cable with the alligator clip (130) to the metal portion of the needle (115) as illustrated by the assembly (140).
3. Connect the connector (133) to an ECG cable.
4. Connect a syringe filled with saline (120) to the hub (Luer lock) (143) of the needle (115).
5. Flush saline from the syringe (120) through the needle (115) and through the catheter (105).

As a result, at the end of this procedure, the metal nipple of the connector (133) connected to the ECG cable makes an electrical connection to the tip of the catheter (105) through the saline solution flushed through the needle (115) and through the lumen of the catheter (105).

Figure 2:
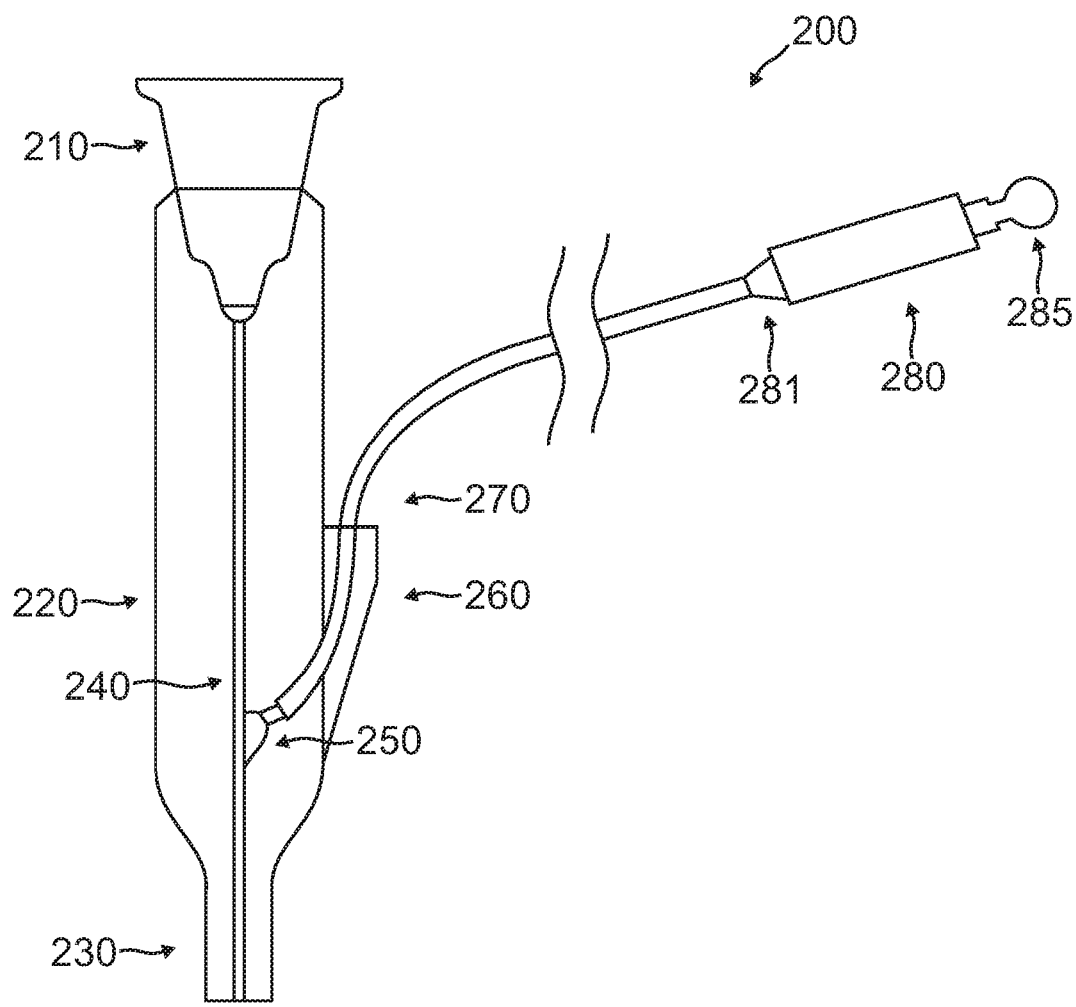
FIG. 2: Embodiment of a device to make an electrical connection to a catheter

FIG. 2 illustrates an embodiment of a device (200) to make an electrical connection to a catheter, to a needle, to the cannula of an implantable port or to other vascular access devices. The device (200) consists of the following parts:
1. A needle (240) made of stainless steel or any other strong cannula made of a biocompatible conductive material with a female Luer lock (210) of any biocompatible material which can be connected to a standard syringe, e.g., PVC or polycarbonate
2. A body of any biocompatible material which can act like an electric insulator, e.g., PVC or polycarbonate, having a male slip connector (230), e.g., a Luer slip. The male slip connector (230) can be inserted into any catheter Luer lock connector. In another embodiment, the slip connector (230) can also be inserted into any cannula of an implantable port or other vascular access device with or without Luer lock. In another embodiment, the male slip connector (230) can be replaced by a male Luer lock.
3. The needle (240) is connected inside the body (220) to an electric wire single or multi-threaded, shielded or non-shielded (270) through the joint (250).
4. The joint (250) between the needle (240) and the un-insulted portion of the cable (270) can be made n different ways, e.g., by using a conductive epoxy, or by solder joint, or by using a heat shrink tube which presses the wire against the needle or by a combination of the above. If the copper or stainless steel wire (270) is shielded, the shield is not connected to the needle.
5. The strain relief (260) for the wire (270). The strain relief can be made from epoxy, from a molded part attached to the wire, from a molded part attached to the body (220), from heat shrink tubing or in a number of other ways.
6. The connector piece (280) is used to connect the device (200) to an ECG cable which has a clip connector. It has an outside body made of electrically insulating material, e.g., PVC. The strain relief (281) supports the wire (270). The nipple formed metal end (285) fits into a connection with a clip ECG cable.
7. In case the cable (270) is shielded, the connector (280) allows for a connection with a shielded ECG cable clip such that the shield of the wire (270) connects to the shield of the shielded ECG cable and the core conductor wire of the wire (270) connects to the core conductor wire of the ECG cable.

In another embodiment, the body (220) can be made of stainless steel or another electrically conductive material. In this embodiment, the electrical joint (250) with the wire (270) can be made by soldering the wire directly on the surface of the body (220). The fluid flowing through the body (220), e.g., saline is in direct contact with the device inner wall, thus electric contact is established between the fluid and the nipple (285).

In another embodiment, the parts (210), (220), and (230) are made of an electrically conductive material, e.g., stainless steel and the needle (240) is missing. The electrically conductive body (220) allows for the fluid to flow directly through a cylindrical longitudinal hole in the center between the female Luer lock (210) to the male slip or male Luer lock (230). In this embodiment, the electrical joint (250) with the wire (270) can be made by soldering the wire directly on the surface of the body (220). The fluid flowing through the body (22), e.g., saline is in direct contact with the device inner wall, thus electric contact is established between the fluid and the nipple (285).

The device (200) can be used in a number of clinical settings in order to allow for ECG-based guidance of catheter placement:

1. In typical situations, an electrolyte like saline solution is flushed into the device through the female Luer lock (210). This is typically achieved by connecting a syringe with saline to the connector (210) and flushing the syringe. Saline can be flushed into the device (200) from other devices than a syringe. For example using a perfusion bag. The Luer connection of a perfusion kit can be connected to the lock (210). With the perfusion stop cock open, a continuous stream of fluid is maintained through the device (200). In another setting, a device like the one described in FIGS. 8 and 9 of the present invention can be attached to the connector (210). In this situation, a continuous flow of fluid is maintained through the device (220). In another situation, a cannula like the one shown in FIG. 7 (755) can be attached to the connector (210). In such a situation, the flow of fluid and air through the device can be obstructed as described in FIG. 7 and continuous fluid pressure can be maintained.
2. In typical situations, the male slip (230) is connected to a Luer lock of a catheter for central venous access, e.g., peripherally inserted central venous catheters (PICC), central venous catheters (CVC), hemodialysis catheters, tunneled catheters, and to the luer lock of the access needle for cannulas of implantable ports. The male slip (230) can also be connected to the device illustrated in FIG. 12 (the Luer lock 1210) of the present invention in order to establish an electrical connection to fluid in the chamber of an implantable port.
3. The electrically conductive nipple (285) can be typically connected to a clip of an ECG cable, which, in turns, can be connected to an ECG monitor or to any other system capable of acquiring patient electrical signals. The conductive nipple (285) can also be connected to the devices illustrated in FIGS. 10 and 11 of the present invention in order to allow for the use by a single sterile operator.
4. In the case of a multi-lumen vascular access device, e.g., a hemodialysis catheter or a multi-lumen PICC, one device (200) can be attached to each of the Luer locks of the vascular access device, thus providing for simultaneous electrical connection to each of the lumens. This situation is particularly important in the case of hemodialysis catheters with staggered tips: electrical signals are simultaneously obtained from each of the catheter tips. Thus the placement of the hemodialysis catheter is very accurate, considering the fact that, in the ideal situation, its two tips must be in different locations: the longer tip in the right atrium and the shorter one at the cavo-atrial junction.

Figure 3:
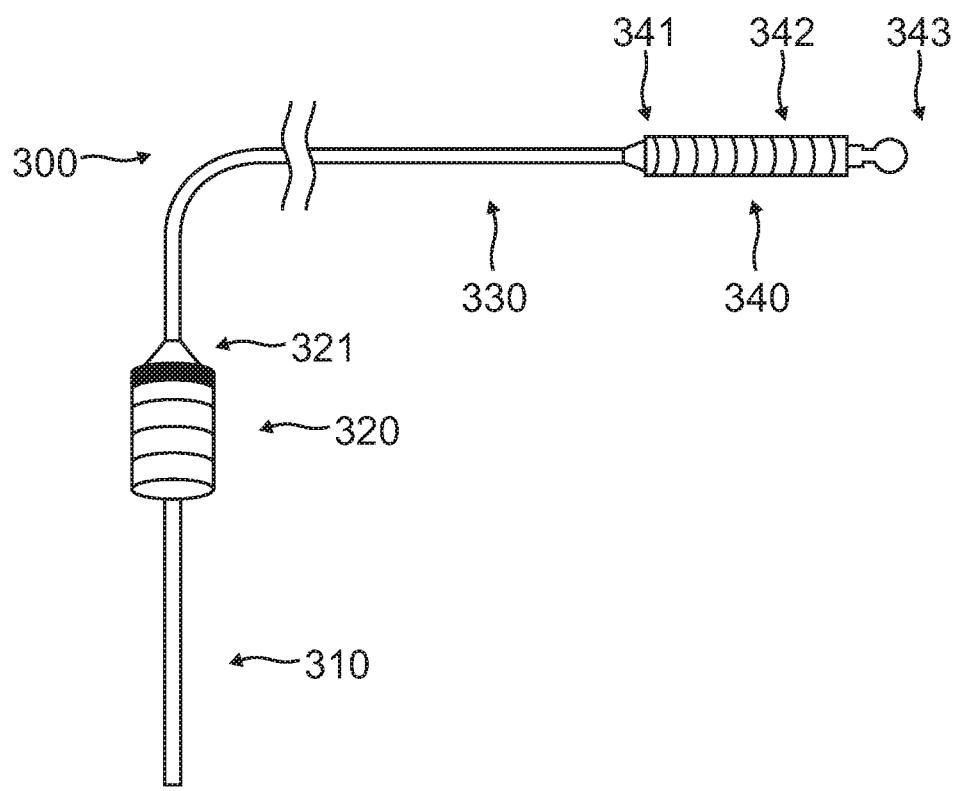
FIG. 3: Device for making an electrical connection to a Luer lock

FIG. 3 illustrates a device for making an electrical connection to a Luer lock. The device (300) is made of the following parts:

1. A metal pin (310). The pin (310) can be made of any biocompatible electrically conductive material, e.g., stainless steel, silver.
2. The metal pin is attached to the wire (330) through a solder joint integrated in the male Luer lock (320).
3. The male Luer lock (320) can be connected to any Luer lock of any catheter or of any other vascular access device, such that the pin enters the lumen of the catheter or of other vascular access devices.
4. The strain relief (321)
5. The connector piece (340) which is used to connect the device (300) to the clip connector of an ECG cable or of any other cable having an appropriate clip connector.
6. The connector piece (340) consists of an insulating body (342), of a strain relief (341) and of a metal nipple connector (343) which makes electrical contact between the wire 330 and any cable with a clip connector which can be clipped on the nipple (343)
7. The wire (330) is made of any electrically conductive material, can be single or multi-threaded and can be shielded or not.

Figure 4:
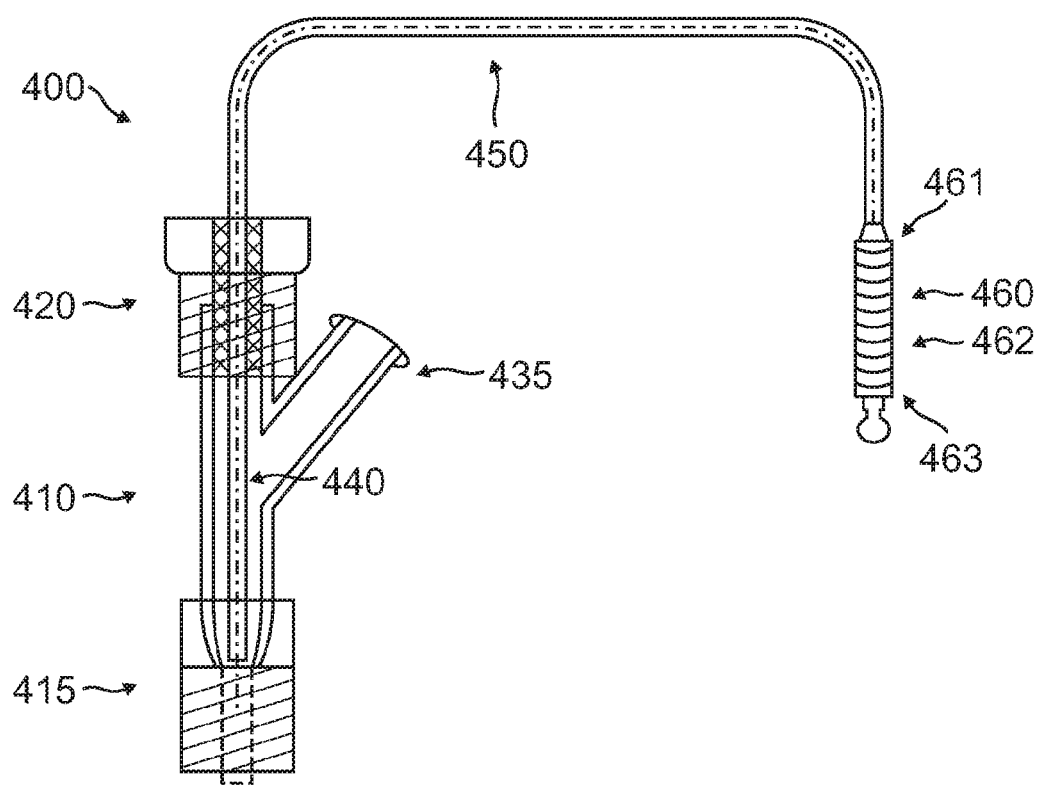
FIG. 4: Another embodiment of a device to make an electrical connection to a catheter

FIG. 4 illustrates another embodiment of a device to make an electrical connection to a catheter. The figure illustrates how the device described in FIG. 3 can be used to provide a new device (400). The device (400) is used to make an electrical connection between a catheter and an electrical cable, e.g., an ECG cable. The device (400) is made of the following parts:

1. A metal pin (440) connected to an electrically conductive wire (450), the join between the pin and the wire being made inside the Luer lock (420).
2. A T- or Y-shaped body (410) with a female Luer slip or lock (420), another female Luer slip or lock (435) and a male Luer slip or lock (415).
3. The female Luer slip or lock (435) can be used to connect a syringe with saline.
4. The male Luer lock or slip (415) can be used to connect the device (400) to a catheter.
5. In another embodiment the device (300) in FIG. 3 can be connected to the female Luer lock (435) and a syringe with saline solution to a female Luer lock corresponding to (420) of the body (410).
6. The wire (450) is connected to the connector piece (460) consisting of an insulating body (462), a strain relief (461), and a metal nipple (463) which can be connected to an electrical cable, e.g., to an ECG cable.

The device in FIG. 4 can be used in similar ways as the device in FIG. 2 if the flush of fluid, e.g., saline or other electrolyte occurs through the port (female Luer lock) (435).

Figure 5:
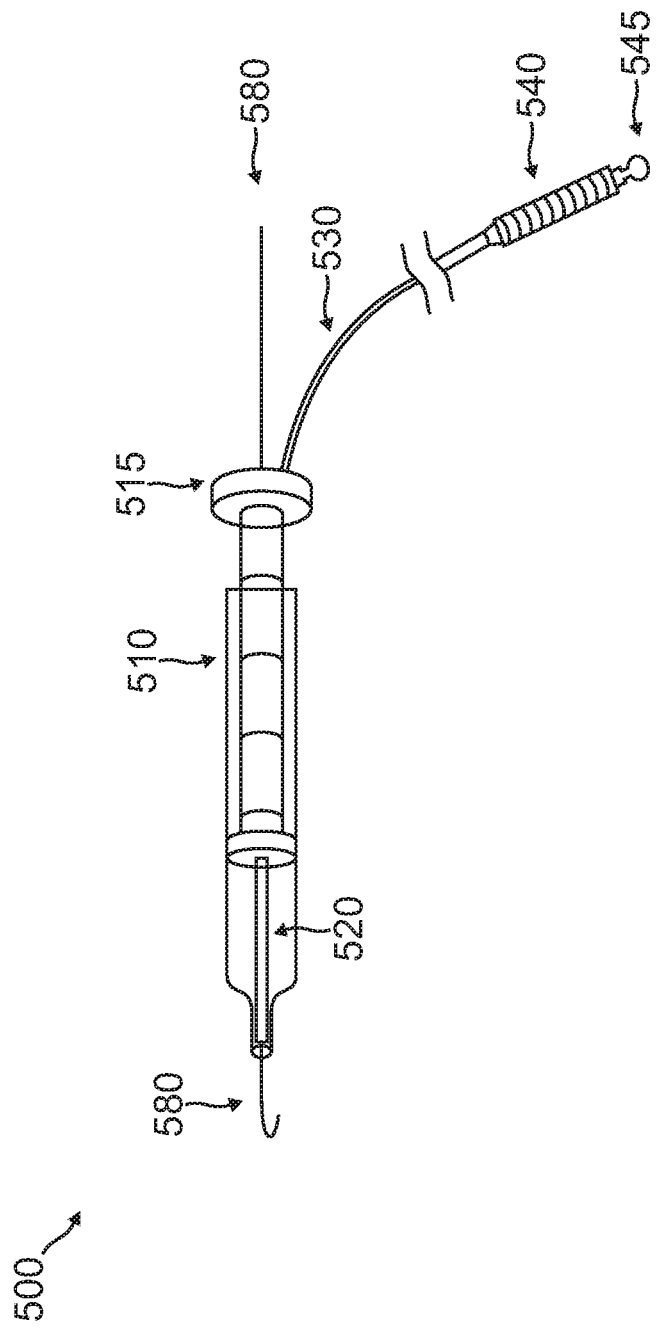
FIG. 5: Syringe with electrical connection

FIG. 5 illustrates a syringe with electrical connection. In order to be able to inject, use a guidewire, and provide an electrical connection at the same time while connected to a catheter, the device (500) consists of the following parts:

1. A syringe (510) having
2. A metal cannula (needle) (520) inside the syringe which passes trough the middle of the piston (515).
3. The needle (520) is made such as to provide a free access pass for a guide wire (580) such that the distal tip of the guidewire (580) can pass inside the needle (520) and exit through the tip of the syringe. The presence of the guidewire (580) inside the needle (520) does not prevent the piston (515) to move along the needle and the syringe to flush fluid through its tip. Thus the syringe can be used while the guidewire is inside the needle.
4. The electrically conductive and insulated wire (530) connected to the inner needle of the syringe at one end and to the connecting piece (540) at the other end.
5. The nipple connector (545) is in electric contact with the needle (520) and thus with the fluid inside the syringe.

The syringe can have a male slip or a Luer lock at its tip. When the syringe is connected to a catheter or to some other vascular access device through a Luer lock or directly into the device cannula, saline solution inside the syringe can be flushed into the catheter ensuring an electric contact between the saline inside the catheter, the saline inside the syringe (510), the needle (520), the wire (530), and the metal nipple connector (545).

At the same time, a guidewire (580) can be inserted through the hollow needle (520) and through an opening in the syringe piston (515) without any impact on the electrical connection established by the saline solution described above (catheter lumen, syringe volume, needle, wire and metal nipple). This configuration is particularly useful in over the wire catheter insertion procedures, e.g., in the insertion of CVCs using guidewires or in the insertion of PICCs using the Seldinger technique.

Alternatively, the device illustrated in FIG. 1 (130) can be connected directly to the proximal end of the guidewire (580) using the alligator clip (131). Thus, an electrical connection is established between the guidewire and the metal nipple (134). When the guidewire is in the vasculature inside a catheter or an introducer such that its distal tip is in contact with blood, an electrical connection is established through the guidewire between the blood at its distal tip and the nipple connector (134).

Similarly, the device illustrated in FIG. 1 (130) can be connected directly to the proximal end of a stylet inside a PICC using the alligator clip (131). Thus, an electrical connection is established between the stylet and the metal nipple (134). When the stylet is in the vasculature inside a catheter such that its distal tip is in contact with blood, e.g., flush with the catheter tip, an electrical connection is established through the stylet between the blood at its distal tip and the nipple connector (134).

In another embodiment, the wire (530) with the connector (540) and the metal nipple (545) can be electrically connected directly to the guidewire (580). In such a situation, the guidewire may provide electrical contact with the inner walls of the needle (520), thus establishing an electrical connection between the saline inside the syringe, the needle, and the metal nipple (545). Another use of a guidewire with electrical connection is to establish an electrical connection between the distal of the guidewire and the metal nipple (545) through the guidewire itself. Such a connection can be useful for ECG-guided navigation of guidewires and/or placement of devices over the guidewire.

FIG. 6 illustrates a valved device (600) for maintaining saline column integrity. The device (600) consists of a body (601) similar to a syringe, which allow for fluid, e.g., saline to flow from the female Luer lock (603) to the male slip or Luer lock (602). Inside the body of the syringe there is a valve (605) and a metal connection (610) making an electrical connection to a wire (611) and a connecting piece (612). The male Luer lock or slip (602) can be connected to a catheter or to any other access device with an appropriate opening, e.g., Luer lock or cannula. The female Luer lock or slip (603) can be connected to a syringe filled with fluid, e.g., saline solution. When the saline is flushed from the syringe into the device body (601) by applying positive pressure, the valve (605) opens, the saline fills the device body and makes contact with the metal piece (610). Further, the saline also flows through the tip (602) into the catheter filling the catheter lumen with saline. Thus electrical contact is ensured between the distal end of the catheter lumen, the contact piece (610) and the connector piece (612). The metal piece (613) of the connector (612) can be connected to an electric cable, e.g., an ECG cable from an ECG monitor.

Figure 6A:
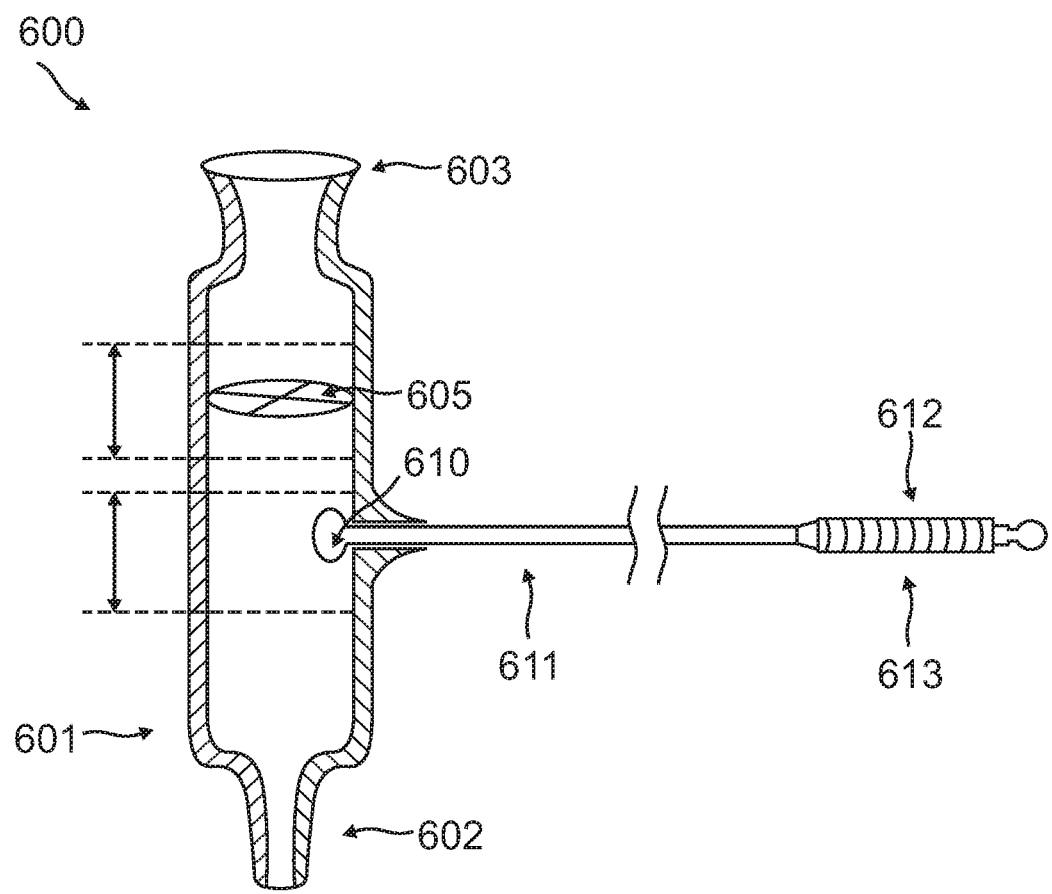
FIGS. 6A-E: Various embodiments of a valved device for maintaining saline column integrity.
Figure 6B:
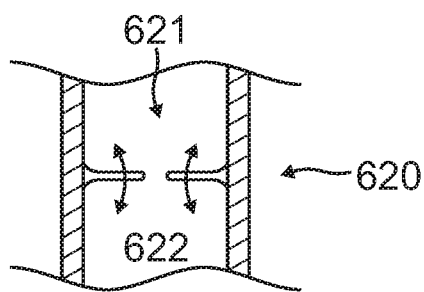
Figure 6C:
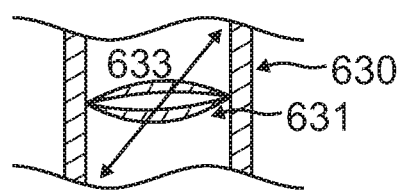

It will be obvious to one of ordinary skill in the art that various embodiments of valve (605) can exist. For example, as illustrated in FIGS. 6A-C, valve (605) can be made of a number of semi-elastic or elastic biocompatible materials, e.g., polyurethane, silicone, PVC. In one embodiment, valve (620) is made of two wings (621) and can open along the longitudinal axis of the device (622). In another embodiment, valve (630) has a slit (631) in the semiplastic material which may open along an axis (633) transverse to the longitudinal axis of the device. In yet another embodiment, a combination of valves may also possible.

Figure 6D:
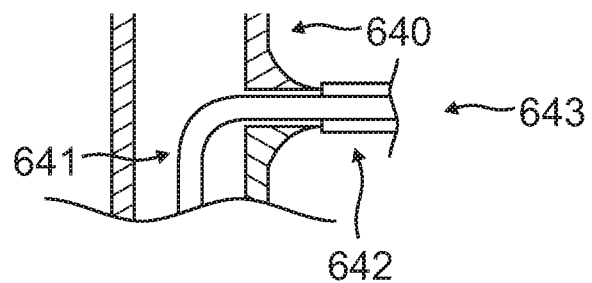
Figure 6E:
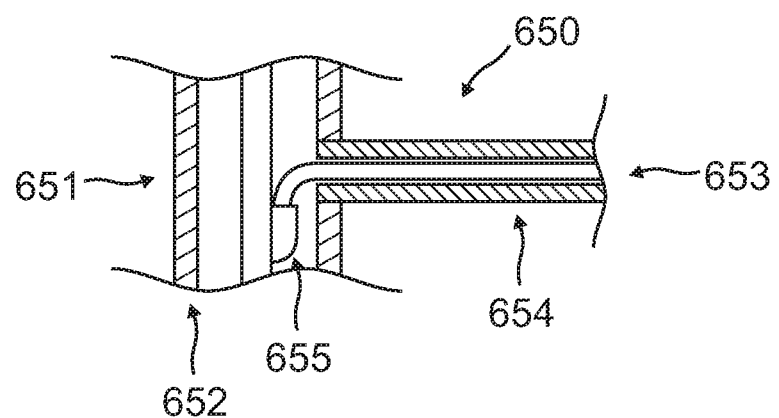

Various embodiments of the metal connection (610) that connects the electrically conductive wire (611) and the fluid inside the device body (601) are contemplated. As illustrated in FIGS. 6D-6E, the metal connection (610) can be shaped in different ways and made of different electrically conductive materials. In one embodiment, illustrated in FIG. 6A, the connection (610) is a spherical or cylindrical shape. In another embodiment, illustrated in FIG. 6D, an un-insulated portion of the wire (641) is in contact with the fluid inside the device body. The wire insulation (642) of the wire (643) is cut such as to allow the proper connection and penetration through the device wall (640). In another embodiment (650), illustrated in FIG. 6E, a needle (652) passes through the device body (651). The fluid, e.g., saline flows inside the needle (652). The electrical joint (655) makes the electrical connection between the needle (652) and the wire (653) with the insulation (654) properly cut to length. In this case the electrical contact to the catheter is made by the saline solution inside the catheter lumen and inside the needle (652) and by the electrical connection between the needle (652) and wire (653).

The valve (605) and its embodiments (620) and (630) are bidirectional. When fluid, e.g., saline is flushed from the syringe-connected end (603) to the catheter-connected end (602) of the device, the valves open as to allow the fluid from the syringe into the catheter. When fluid, e.g., blood, is drawn from the catheter-connected and (602) into the syringe through the syringe-connected end (603) by applying negative pressure, the valves open such as to allow the flow of blood from end (602) to (the end (603).

When no fluid is flushed into the catheter or drawn from the catheter, i.e., when no pressure is applied to valve, the valve is closed. By maintaining a closed valve and thus avoiding any changes in pressure, the integrity of the saline column can be maintained in the catheter lumen. Thus, the integrity of the electrical connection provided by the saline column between the distal tip of the catheter and the metal connector (610) can be maintained. Thus the need to reflush saline from the syringe in order to ensure electrical conductivity is diminished.

FIG. 7 illustrates a method for maintaining saline column integrity. A clip (700) is used selectively enable or block the flow of fluid through a cannula, e.g., through a catheter. The clip (700) is made of a semi-elastic material as shown by (710). The cannula or catheter is passed through the hole (715) with the help of the moving part (716). When a catheter or cannula (755) passes through the hole (715), the flow of fluid through the cannula, e.g., saline, coming from a syringe (770) through the needle (765), is not obstructed. By pushing the cannula into the pointed end (760) of clip (700), the flow of fluid through the cannula (755) can be obstructed or stopped.

In another embodiment, a connective device as in FIGS. 1, 2 and 4 can be used to connect the cannula (755) to a catheter. After saline has been flushed into the device and into the catheter, the piece (760) is pushed as to obstruct the fluid path from the syringe. The fluid column which was flushed into the cannula, into the connecting device and into the catheter lumen is isolate from any change in pressure due to the obstruction of the cannula using the piece (760). Because the saline column is not subject to any pressure changes, its integrity is maintained. Thus the integrity of the electrical connection between the ECG cable connector of the devices in FIGS. 2 and 4 and the distal tip of the catheter through the saline column can be maintained.

FIG. 8 illustrates a device for opening the distal valves of a catheter using saline. In the situation in which catheters have distal valves, for example Groshong catheters, constant pressure is required to maintain the valves open. Maintaining the valves open is important so that there is contact between the blood outside the catheter and the saline solution inside the catheter. The contact between blood and saline through the open valve ensures that electrical contact is established at the distal tip of the catheter between blood and saline. Thus electrical contact is established through the saline solution in the catheter lumen from the blood at the distal tip to the proximal end of the catheter lumen. Using a device as shown in FIG. 1, 2, 4 or 6, an electrical connection can then be established between the proximal end of the catheter and an ECG cable, i.e., and ECG monitor. As a result, the electrical signal at the distal valved end of the catheter can be captured by the ECG monitor by maintaining the distal valves open.

In FIG. 8 a syringe (810) is used to flush a connecting device like the ones in FIG. 1, 2 and a catheter with saline. The end of the syringe body and the piston handle are positioned in a device (820) as illustrated in FIG. 8. The device (820) includes a spring (840) encapsulated in a protective material (830). In the initial position the syringe piston is next to the syringe volume, the volume of the fluid in the syringe is minimal, and the spring is relaxed. When drawing saline into the syringe, the spring element (840) extends (direction 1). When releasing the piston, the spring element tends to retract (direction 2) back to its default position, thus causing the piston of the syringe to flush the saline. Thus, continuous pressure is applied to the piston, which continuously releases saline from the syringe into a connecting device (FIG. 1, 2, 4) and into a catheter with distal valves. Through the continuous push/flush the catheter valves remain open, thus ensuring continuous electrical contact between the connecting device (FIG. 1, 2, 4) and the blood at the distal end of the catheter.

The devices in FIGS. 8 and 9 can be used to obtain continuous flushing for other clinical applications as well, when such a continuous flush is desired.

FIG. 9 illustrates another embodiment of a device for opening the distal valves of a catheter using saline. In FIG. 9 the device containing a syringe (910) can be connected to a catheter or to a connecting device (FIGS. 1, 2, 4) with its male Luer slip or lock end (905). Another cylinder (940) acts like a compression cylinder. When the piston (920) of the syringe (910) is retracted as to draw saline (direction 1), the piston 930 is compressing the air in the cylinder (940). The rigid connection (980) ensures that piston (920) retracts at the same time that piston (930) compresses the air within cylinder (940). After the saline has been drawn into syringe (910) and the air in syringe (940) is compressed, the lock (960) is rotated to position 3 so as to block the movement of the piston head (925). In the filled and compressed position, the device is connected to a connecting device (FIGS. 1, 2, 4) and the lock (960) is rotated to position 4 so as to allow movement of piston head (925). As a result of pressure applied by the compressed air (or liquid) in the cylinder (940) when releasing the lock (960), the piston (920) will be pushed in direction 2 and thus, the syringe (910) will be flushing saline into the device connected to luer lock (905). In this manner a continuous flush is achieved which maintains the valves of a catheter in an open position for the period of time in which the air in cylinder (940) is decompressing.

Figure 10A:
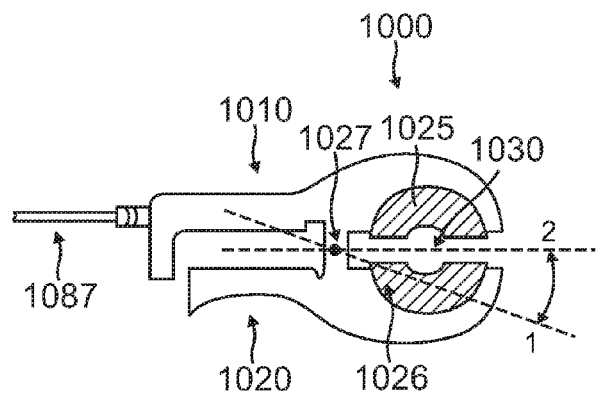
FIGS. 10A-C: Various embodiments of a device for connecting sterile and non-sterile cables by a sterile operator.
Figure 10B:
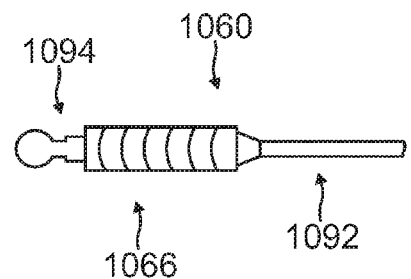
Figure 10C:
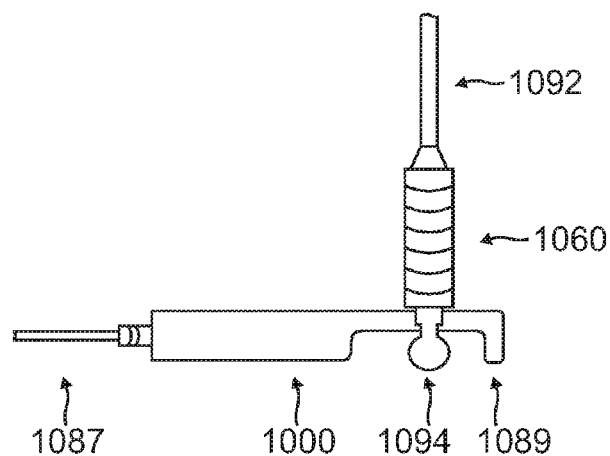

FIGS. 10A-C illustrate a device for connecting sterile and non-sterile cables by a sterile operator. A clip connector (1000) is the clip end of an ECG cable the opposite end of which may be connected to an ECG monitor, and is non-sterile. The device (1060) is the connector end of a device similar to those in FIGS. 1, 2, 4, 6 and is sterile. FIG. 10 C illustrates a side view of how the connector (1060) can be connected to the clip connector (1000). The clip connector (1000) has a resting edge (1089) which maintains the device in a horizontal, stable position when the nipple (1094) is pushed in between the metal plates (1025) and (1026) thus making an electrical connection between wire (1092) and wire (1087).

The clip connector (1000) consists of the following parts:

1. A shielded cable, or wire (1087) which can be connected to an ECG monitor or equivalent system for the acquisition of electrocardiographic signals.

2. A first plastic (or any other hard enough electrically isolating material) handle (1010) and a second plastic handle (1020) which can pivot, about position (1027), towards and away from each other generally between axis 1 and axis 2. Handles (1010, 1020) are made of such materials as to be able to move between axis 1 and axis 2 when pressed and are then able to return to the initial position (illustrated in FIG. 10A) when released. In another embodiment, a spring (not shown) can be inserted between the handles (1010, 1020) such as to aid in the movement of the two handles with respect to each other. The movement of the two handles can occur when either:

a. Handle (1020) is pressed towards handle (1010) or b. The metal nipple (1094) of the connector (1060) is pressed into the hole (1030) formed between metal plates (1025, 1026).

3. The metal (or any other hard enough electrically conductive material) plates (1025) and (1026) are fixed to handles (1010) and (1020) respectively.

The connecting piece (1060) consists of an electrically insulating handle (1066), a wire (1092), and a nipple metal connector (1094) connected to the wire (1092) inside the handle (1066).

FIG. 10 C illustrates a side view of the device when the metal nipple (1094) of the connector (1060) has been inserted in between metal plates (1025, 1026) of the connector (1000). The connector (1000) has a resting edge (1089) which provides the required resistance when the connector (1060) is pressed into the connector (1000).

The device illustrated in FIGS. 10A-C can be used by a single sterile operator to establish an electric contact to a catheter as follows:

1. While still non-sterile, the single operator connects the non-sterile cable (1087) to the system used for monitoring the patient's electrical signals, e.g., to an ECG monitor, and places the clip piece on an accessible surface.

2. While doing the sterile procedure, the single operator takes the sterile connector (1060) and with a single sterile hand pushes the nipple metal piece (1094) in the hole (1030) between the metal plates (1025) and (1026) without touching any non-sterile element.

Figure 11A:
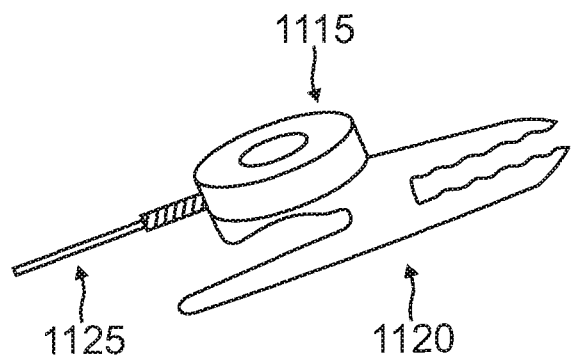
FIGS. 11A-C: Various embodiments of a device for connecting sterile and non-sterile cables by a sterile operator.
Figure 11B:
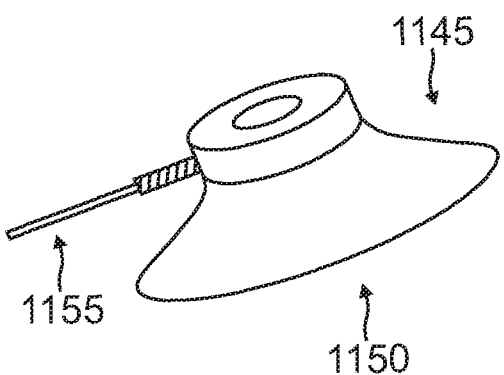
Figure 11C:
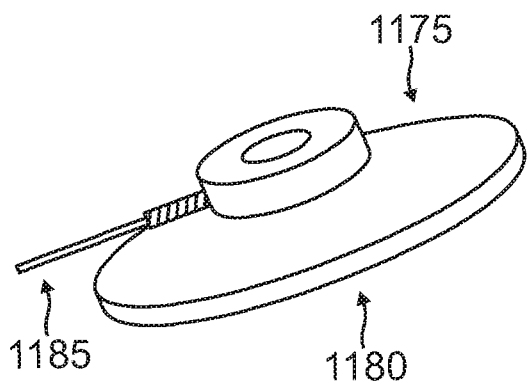

FIGS. 11A-C illustrate various embodiments of a device for connecting sterile and non-sterile cables by a sterile operator.

In one embodiment, illustrated in FIG. 11A, an alligator clip (1120) is attached to a snap connector (1115). The cable (1125) can be connected to an ECG monitor. The alligator clip (1120) can be clipped to elements in the patient environment which are close to the patient, e.g., drapes. A non-sterile operator can fix the non-sterile snap connector (1115) in a convenient position and location before the procedure. During the procedure, a sterile operator can push the sterile nipple (not shown) of a connector piece, similar to those shown in FIGS. 1, 2, 4, 5, 6, into the snap connector (1115) using a single hand and without having to leave the sterile field.

In another embodiment, illustrated in FIG. 11B, a snap connector (1145) can be connected to an ECG monitor through the cable, or wire (1155). Attached to the snap connector (1145) there is a suction cup (1150). The suction cup serves the purpose of fixing the snap connector (1145) in a convenient position and location such that a sterile operator can connect a metal nipple end (not shown) of a connector piece, similar to those shown in FIGS. 1, 2, 4, 5, 6, with the snap connector (1145).

In another embodiment, illustrated in FIG. 11 C, a snap connector (1175) can be connected to an ECG monitor through a cable, or wire (1185). Attached to the snap connector (1175) there is a plastic or metal disc (1180). The disc serves the purpose of supporting the snap connector (1175) in a convenient position and location such that a sterile operator can connect a metal nipple end (not shown) of a connector piece, similar to those shown in FIGS. 1, 2, 4, 5, 6, with the snap connector (1145).

Figure 12:
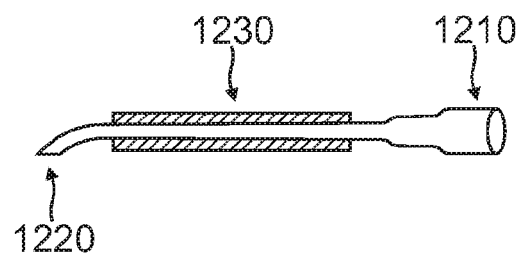
FIG. 12: Needle for ECG-capable access of implantable ports

FIG. 12 illustrates a needle for ECG-capable access of implantable ports. The needle is made of metal, e.g., stainless steel, it has a distal pointed curved end (1220). The plane of the needle opening (1220) is oriented parallel to the needle long axis in order to minimize the damage which the needle may produced when introduced into the valve (1510) of an implantable port like the one shown in FIG. 15. The needle has a female Luer lock end (1210) to be connected to a syringe. The needle is covered with an electrical insulation (1230) for the most part of its length such that the curved tip and approximately 1 cm of length towards the needle's Luer lock end are exposed to electrical contact. The insulation (1230) can be obtained by coating the needle with an electrically non-conductive coating. Alternatively, the insulation (1230) can be made out of a thin plastic tubing which fits over the needle and does not change the needle's penetration capability.

The needle illustrated in FIG. 12 can be used to support the ECG method of verification of the tip location of the catheter connected to the implantable port. A device as those shown in FIGS. 1, 2, 4, 5, 6 can be connected to the Luer lock of the needle making an electrical connection to the needle. Alternatively, an electrical cable with an alligator clip like the one described in FIG. 1 (130) can be connected to the non-insulated part of the needle making an electrical connection to the needle. This electrical connection can be then connected to an ECG monitor.

In order to support the ECG method for catheter tip location, the implantable port in which the needle is inserted must be electrically insulated from the patient's body. This insulation can be obtained with the device described in FIG. 15. An implantable port made of plastic or other non electrically conductive materials can also be used. The location of the tip of a catheter connected to such an implantable port can be determined using the ECG method and the needle described herein during the placement procedure and also post-procedurally, for example each time that the port is used. Alternatively, the implantable port can be electrically insulate from the patient's body by placing the implantable port during the procedure and before final implantation on an electrical insulator like a piece of sterile gauze, cotton, drape or alike.

Figure 13:
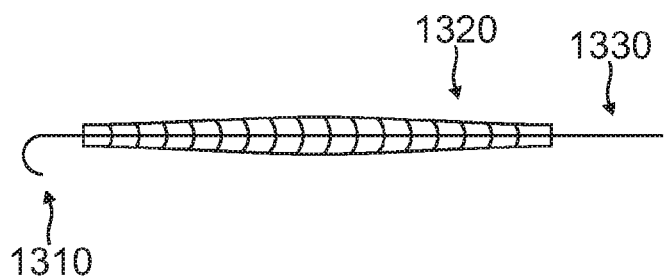
FIG. 13: Device for isolating and marking of guidewires

FIG. 13 illustrates a device for electrically insulating and marking guidewires. Any guidewire made of electrically conductive material can be used to support ECG-based guidance if the surface of the guidewire is electrically insulated for its entire length except for its distal (1310) and proximal tips (1330). The insulation (1320), illustrated in FIG. 13, consists of a thin tube of biocompatible material, e.g., PVC, polyurethane, silicon which is extruded at such a thickness as to not influence the guidewire's ability to pass through any intended vascular access device, e.g., introducers and needles. The thin insulation tube is marked with markings (e.g. centimeters), such that the operator knows what the length of the inserted portion of the device is. The distal tip of the guidewire is in contact with blood while at the proximal end of the guidewire, a connecting device like the one illustrated in FIGS. 1A-C (130) can be connected. Thus, an electrical connection can be established between the distal tip of the guidewire, its proximal end and an ECG monitor. The ECG guiding method can be applied to determine the location of the guidewire tip.

Figure 14:
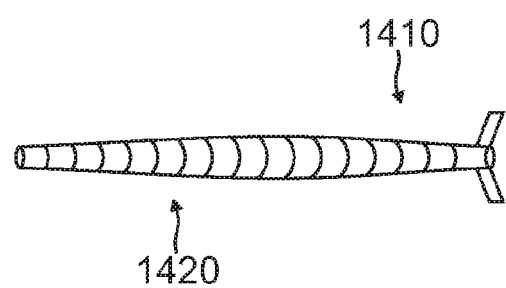
FIG. 14: ECG-capable introducer with markings

FIG. 14 illustrates ECG-capable introducer (1410) with markings (1420). A marked introducer, e.g., with centimeter markings, can be used to assess the tip location of vascular access devices like guidewires and catheters in ECG-based guidance. A marked introducer acts like a marked sleeve for the guidewire or catheter introduced in the blood vessel through the introducer when the tips of the two devices are aligned. Thus, using a device as shown in FIGS. 1, 2, 4, 6 to make an electrical connection to a catheter or guidewire placed through a marked introducer provides ECG-base information about the catheter or guidewire tip location in reference to the markings on the introducer. In particular a centimeter marked introducer is useful when the guidewire is placed under ECG guidance and then a catheter is placed at the same desired location through the same introducer.

Figure 15:
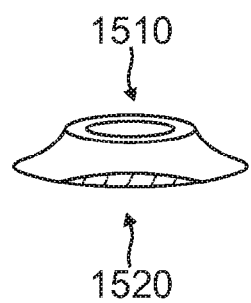
FIG. 15: Insulated implantable port and method for ECG-guided implantable port placement
Figure 16A:
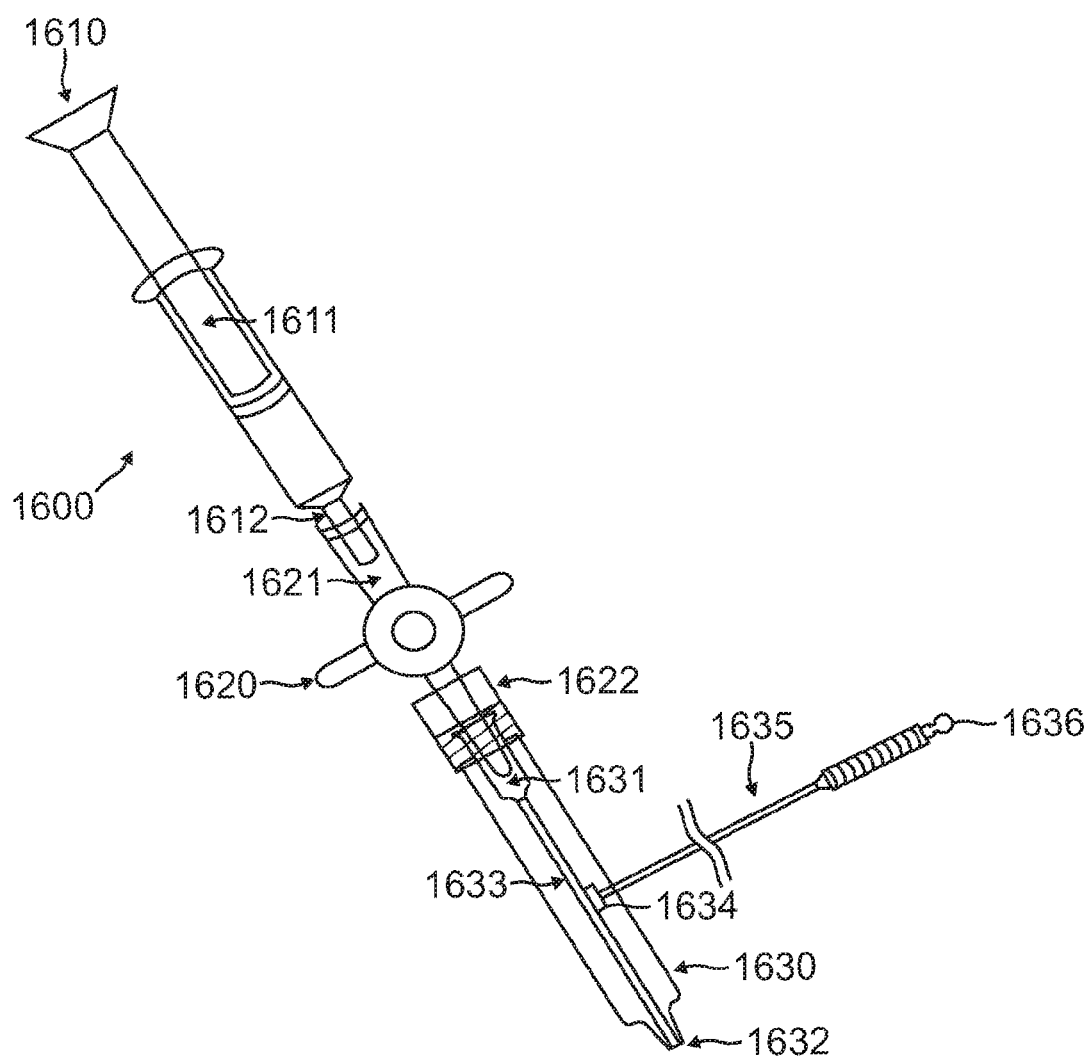
FIGS. 16A-D: Device and method for making an electrical connection to a catheter using saline solution and ensuring saline column integrity.
Figure 16B:
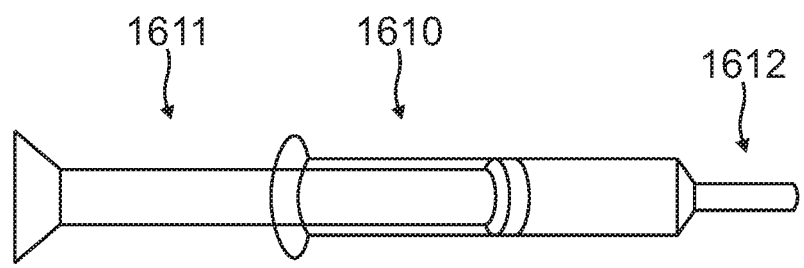
Figure 16C:
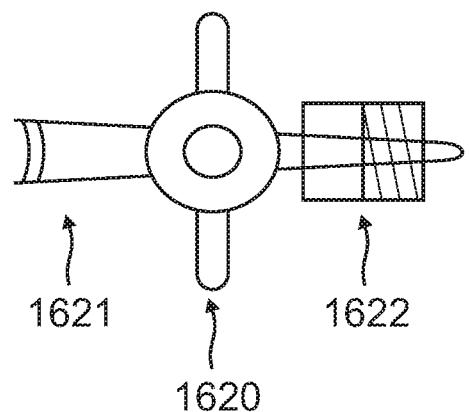
Figure 16D:
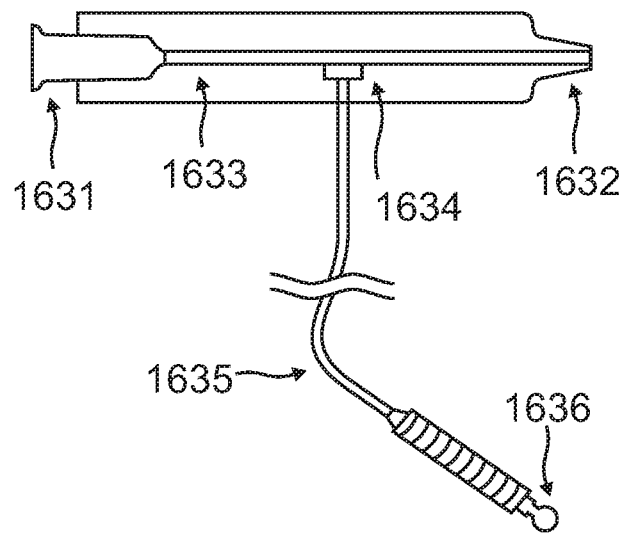

FIG. 15 illustrates an insulated implantable port (1510) with an insulated base (1520) and a method for ECG-guided implantable port placement. The ECG method can be applied for guiding the placement of catheters connected to implantable ports if a connecting device according to the present invention (FIGS. 1, 2, 4, 6) is connected directly to the port catheter, to a needle used to flush the catheter, or to the needle in FIG. 13 used to access the port chamber. In addition, the port itself must be electrically insulated from the patient body. The electrical insulation can be achieved either by making the port from electrically non-conductive materials or by coating the metal base (1520) with an electrically insulating coating. In such a case, the verification of the catheter tip placement can be achieved during the placement procedure and at any time post-procedurally.

FIGS. 16A-D illustrate a method to make an electrical connection to a catheter, to a needle, to the cannula of an implantable port or to other vascular access device and to maintain the saline column integrity during the procedure.

The device (1600) to be used with the method consists of the following parts:

1. A syringe (1610). The syringe (1610) has a piston (1611) and male slip (1612).

2. A stopcock (1620) with luer connection with one way male lock, is connected with its female luer (1621) to the male slip of the syringe. At an opposite end of stopcock (1620) from the female luer (1621) the male luer lock (1622) is connected to the female luer lock (1631) of the device 1630.

3. A device (1630) similar to the one described in FIG. 2. This device is intended to make an electrical connection to a catheter, to a needle, to the cannula of an implantable port or to other vascular access devices. The female luer (1631) of this device is connected to the male slip of the stopcock with luer connection (1622). The male slip connector (1632) is connected to a catheter, to a needle, to the cannula of an implantable port or to other vascular access devices. The needle or electrically conductive cannula (1633) allows for the flow of electrolyte, e.g., saline from the syringe into the device connected to the male slip (1632). Alternatively, the male slip (1632) can also be made as a male Luer lock. The electrical joint (1634) makes an electrical connection between the metallic cannula (1633) and the wire (1635). The wire (1635) is electrically connected to the metal nipple of a connector (1636). The metal nipple (1636) can be connected to a clip or snap connector of a cable making connection to an ECG monitor or to any other system capable of acquiring patient electrical signals.

4. In different embodiments, the syringe (1610) and the stopcock (1620) can be used with other devices than the device (1630) which provide an electrical connection between to the fluid flowing through the device. Instead of the device (1630), for example, the devices illustrated in the present invention in FIGS. 1 (140) and 4 can be used.

The method can be used in a number of clinical settings in order to allow for ECG-based guidance of catheter placement and it consists of the following steps:

1. The device (1630) or a similar device (FIG. 1 (140) or FIG. 4) is connected with its male slip (1632) to the catheter Luer lock.
2. The metal nipple (1636) is connected to a system capable of acquiring electrical signals, e.g., an ECG monitor.
3. The stopcock (1620) is connected using the Luer lock (1622) to the Luer lock (1631) of the device (1630).
4. The syringe (1610) is filled with saline and then connected to the Luer lock (1621) of the stopcock.
5. The stopcock is turned to the open position as to allow to fluid flow from the syringe into the device (1630) and into the catheter.
6. Saline is flushed from the syringe into the catheter such that the catheter lumen is filled with saline.
7. Once the catheter lumen is filled with saline, the stopcock is turned in the "closed" position. Thus, the pressure inside the saline column remains unchanged and the integrity of the electrical connection established through the column of saline and the wire (1635) between the tip of the catheter and the nipple connector (1636) is maintained throughout the procedure.

In one embodiment of the method, the catheter is introduced in the patient vasculature first, and then the proximal end of the catheter is connected to the device (1620). In another embodiment of the method, the catheter is first connected to the device (1620) and then introduced in the patient's vasculature.

What is claimed is:

1. A device for ECG guided vascular access, comprising:
    an electrically conductive cannula, with a first cannula end and a second cannula end;
    a body, extending from the first cannula end to the second cannula end, having a wall thickness that is greater than a wall thickness of the electrically conductive cannula;
    the first cannula end configured to be connected with a vascular access device;
    the second cannula end configured to be connected to a syringe; and
    an electrically conductive wire with a first wire end and a second wire end, the first wire end being coupled to the electrically conductive cannula, and the second wire end including a nipple connector.

2. The device according to claim 1, wherein at least a portion of the body is electrically insulated.

3. The device according to claim 1, wherein the nipple connector is connected to an ECG data acquisition system.

4. The device according to claim 3, wherein the ECG data acquisition system is an ECG monitor.

5. The device according to claim 2, wherein the body covers at least a portion of the electrically conductive wire.

6. The device according to claim 2, wherein the body comprises a first section and a second section.

7. The device according to claim 6, wherein the first body section and the second body section are separable along a plane substantially parallel with an axis of the electrically conductive cannula.

8. The device according to claim 7, wherein the first body section and the second body section enclose a circumference of the electrically conductive cannula.

9. The device according to claim 1, wherein the electrically conductive wire is coupled to the electrically conductive cannula by an electrically conductive means selected from the group consisting of soldering, laser welding, ultrasound soldering, gluing, and crimping.

* * * * *